US010127360B2

(12) United States Patent
Chack et al.

(10) Patent No.: US 10,127,360 B2
(45) Date of Patent: Nov. 13, 2018

(54) MATERIAL DISPENSER AND NOTIFICATION SYSTEM

(71) Applicant: FirstEnergy Ventures Corp., Akron, OH (US)

(72) Inventors: Dennis Marshall Chack, Akron, OH (US); Brett William Reynolds, Medina, OH (US); Michele Domiano Jones, Hinckley, OH (US); Amanda Marie Kidder, Akron, OH (US); Timothy William Wechter, Akron, OH (US); David Lynn Griffing, North Canton, OH (US); Lauren Rae Lucas, Youngstown, OH (US); Josh Ryan Schulte, North Canton, OH (US); Cheryl Ann Brubaker-Schaub, Wadsworth, OH (US); Kenneth Michael Burns, Akron, OH (US); James Thomas Petroski, Parma, OH (US); Benjamin Back Rose, Akron, OH (US); Carl Anthony Shotwell, Cleveland, OH (US); William Bagnal Timms, III, Medina, OH (US); Jon Eric Washington, Clinton, OH (US)

(73) Assignee: FirstEnergy Ventures Corp., Akron, OH (US)

( * ) Notice: Subject to any disclaimer, the term of this patent is extended or adjusted under 35 U.S.C. 154(b) by 0 days.

(21) Appl. No.: 15/484,826

(22) Filed: Apr. 11, 2017

(65) Prior Publication Data

US 2017/0293741 A1    Oct. 12, 2017

Related U.S. Application Data

(60) Provisional application No. 62/320,792, filed on Apr. 11, 2016, provisional application No. 62/321,260, (Continued)

(51) Int. Cl.
*G06F 19/00* (2018.01)
*A61J 7/04* (2006.01)
(Continued)

(52) U.S. Cl.
CPC ........ *G06F 19/3462* (2013.01); *A61J 7/0076* (2013.01); *A61J 7/04* (2013.01);
(Continued)

(58) Field of Classification Search
CPC ........ G06F 19/3462; G06F 21/40; A61J 7/04; A61J 7/0481; A61J 7/0076
(Continued)

(56) References Cited

U.S. PATENT DOCUMENTS 5,912,818 A * 6/1999 McGrady ................ G06M 7/04
  700/214
5,957,372 A * 9/1999 Dean ....................... G07F 7/069
  221/9

(Continued)

*Primary Examiner* — Michael Collins
(74) *Attorney, Agent, or Firm* — Tucker Ellis LLP; Heather M. Barnes; Michael G. Craig

(57) ABSTRACT

A system for medicine dosage compliance may comprise a dispensing component that provides for medicine to be dispensed based at least upon authorized identification of a user and a secondary authorizer. The dispensing component may comprise an identity authentication component that automatically authenticates an identity of the user and the secondary authorizer at the time of a dispensing event. The system may further comprise a communication component providing one or more notifications to one or more third parties. The communication component may comprise a wireless personal area networking component that sets up a local networking connection between the dispensing component and a local device to share data between the dispensing component and a local device. The local device may communicatively be coupled to a remote network compo-
(Continued)

nent. A notification component may generate notification information of the dispensing event for one or more third parties.

17 Claims, 15 Drawing Sheets

Related U.S. Application Data filed on Apr. 12, 2016, provisional application No. 62/323,091, filed on Apr. 15, 2016, provisional application No. 62/323,640, filed on Apr. 16, 2016.

(51) Int. Cl.
| | |
|---|---|
| *H04W 4/00* | (2018.01) |
| *G06F 21/32* | (2013.01) |
| *G06F 21/40* | (2013.01) |
| *H04W 4/80* | (2018.01) |
| *A61J 7/00* | (2006.01) |
| *G06F 21/62* | (2013.01) |
| *G06Q 10/10* | (2012.01) |
| *G16H 10/60* | (2018.01) |

(52) U.S. Cl.
CPC ............ *A61J 7/0481* (2013.01); *G06F 19/00* (2013.01); *G06F 21/32* (2013.01); *G06F 21/40* (2013.01); *H04W 4/80* (2018.02); *A61J 2200/30* (2013.01); *G06F 19/328* (2013.01); *G06F 21/6245* (2013.01); *G06Q 10/109* (2013.01); *G16H 10/60* (2018.01)

(58) Field of Classification Search
USPC .......................................... 700/236, 237, 244
See application file for complete search history.

(56) References Cited

U.S. PATENT DOCUMENTS

| | | | | |
|---|---|---|---|---|
| 5,961,036 | A * | 10/1999 | Michael | G07F 7/069 221/9 |
| 6,788,997 | B1 * | 9/2004 | Frederick | G06F 19/3462 700/236 |
| 8,588,966 | B2 * | 11/2013 | Michael | A61J 7/0084 221/122 |
| 8,849,445 | B2 * | 9/2014 | Holmes | G07F 17/0092 700/213 |
| 2008/0119958 | A1 * | 5/2008 | Bear | A61J 7/0481 700/244 |
| 2010/0114367 | A1 * | 5/2010 | Barrett | G06F 19/3456 700/236 |
| 2011/0054678 | A1 * | 3/2011 | Thompson | G06Q 30/06 700/237 |
| 2013/0110283 | A1 * | 5/2013 | Baarman | A61J 7/0084 700/236 |
| 2014/0278510 | A1 | 9/2014 | McLean et al. | |
| 2016/0287480 | A1 | 10/2016 | Hancock et al. | |

* cited by examiner

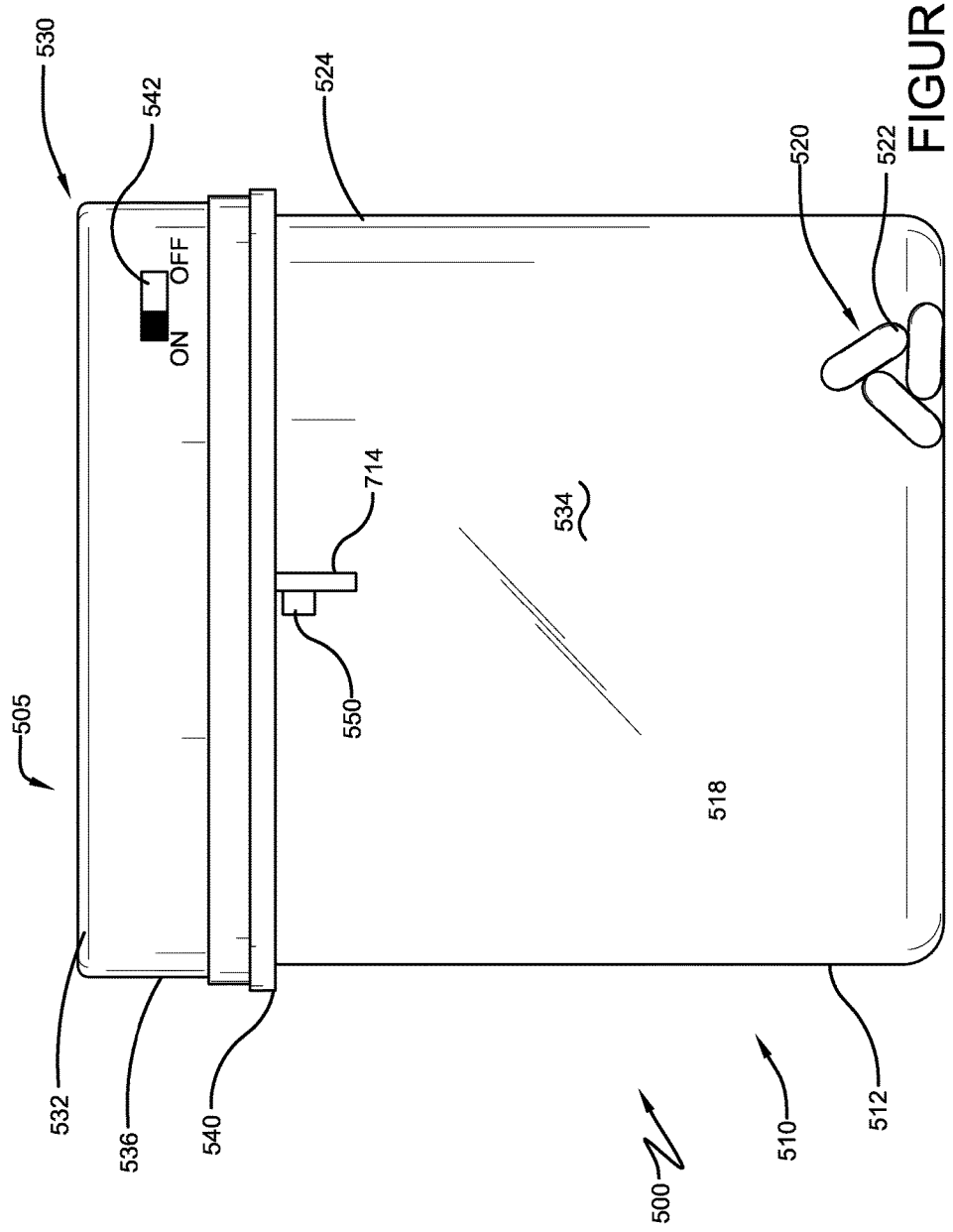

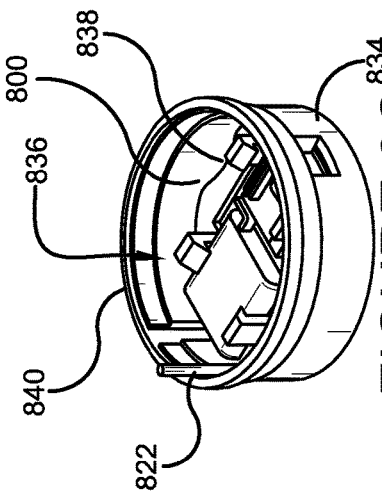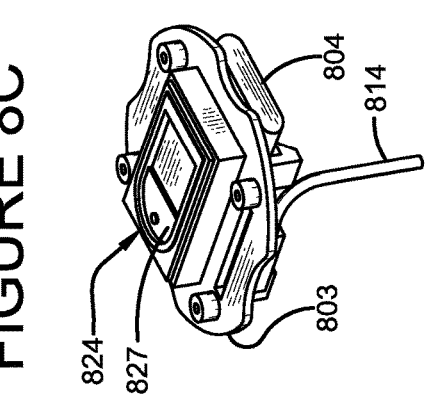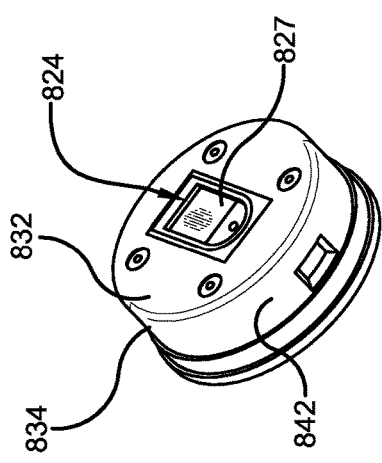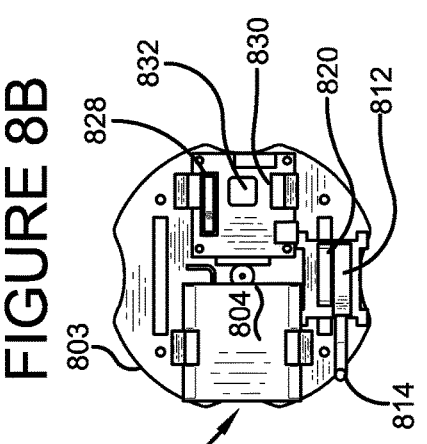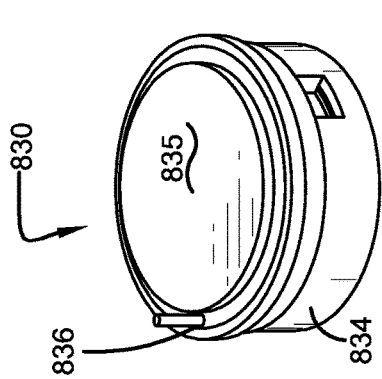
FIGURE 8C
FIGURE 8F
FIGURE 8B
FIGURE 8E
FIGURE 8A
FIGURE 8D

MATERIAL DISPENSER AND NOTIFICATION SYSTEM

CROSS-REFERENCE TO RELATED APPLICATIONS

This application claims priority to U.S. Ser. No. 62/320,792, entitled CONTAINER CAP WITH DATA, SECURITY AND APPROVAL AUTHENTICATION FEATURES, filed Apr. 11, 2016; to U.S. Ser. No. 62/321,260, entitled MATERIAL DISPENSING BAND WITH INDICATOR, DATA RECORDING, AND DATA TRANSMISSION, filed Apr. 12, 2016; to U.S. Ser. No. 62/323,091, entitled MATERIAL DISPENSING BAND WITH INDICATOR, DATA RECORDING, AND DATA TRANSMISSION, filed Apr. 15, 2016, and to U.S. Ser. No. 62/323,640, entitled MATERIAL DELIVERY METHOD AND NOTIFICATION SYSTEM, filed Apr. 16, 2016; all of which are incorporated herein.

BACKGROUND

Patient care is increasingly complex with today's regulatory requirements and sophisticated treatment regimes, in addition to increasing health care costs. As part of this complex scheme is the ability improve the chance that a patient is taking medication as prescribed. Often, caretakers and healthcare providers rely on the patient to follow-the prescribed medication schedule. In some cases, automatic alert systems may provide dosage alerts to a patient, and/or may provide a simple message that a dose has been missed, such as to a caretaker.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As described herein systems and techniques for proving improved patient care by integrating a patient's medicine intake (e.g., or non-medical substance intake) with appropriate communications to interested parties about a patient's medication schedule; including caretakers, doctors, nurses, nurse practitioners, pharmacists, other clinicians, or other health care providers. As an example, an automated system may provide for appropriate dosage to a user patient, based on identification of the user, and other parameters provided by the prescription information, or other information regarding dosage events. In this example, notifications of access to the dosing unit, missed doses, and other appropriate events can be sent out to a network of interested parties associated with the user.

In one implementation, a system for medicine dosage compliance may comprise a dispensing component that provides for medicine to be dispensed based at least upon authorized identification of a user and a secondary authorizer. The dispensing component may comprise an identity authentication component that automatically authenticates an identity of the user and the secondary authorizer at the time of a dispensing event. The system may further comprise a communication component providing one or more notifications to one or more third parties. The communication component may comprise a wireless personal area networking component that sets up a local networking connection between the dispensing component and a local device to share data between the dispensing component and a local device. The local device may communicatively be coupled to a remote network component. A notification component may generate notification information of the dispensing event for one or more third parties.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein:

FIG. 5 is a front elevational view of one aspect of one or more portions of one or more systems described herein.

FIG. 8A is a top perspective view of another implementation of the present invention.

FIG. 8B is a top perspective view of another implementation of one or more portions of one or more systems described herein.

FIG. 8C is a bottom perspective view of one or more portions of one or more systems shown in FIG. 8A.

FIG. 8D is a bottom perspective view of one aspect of one or more portions of one or more systems described herein.

FIG. 8E is a bottom view of one or more portions of one or more systems shown in FIG. 8A.

FIG. 8F is a top perspective view of one or more portions of one or more systems shown in FIG. 8A.

DETAILED DESCRIPTION

Figure 1:
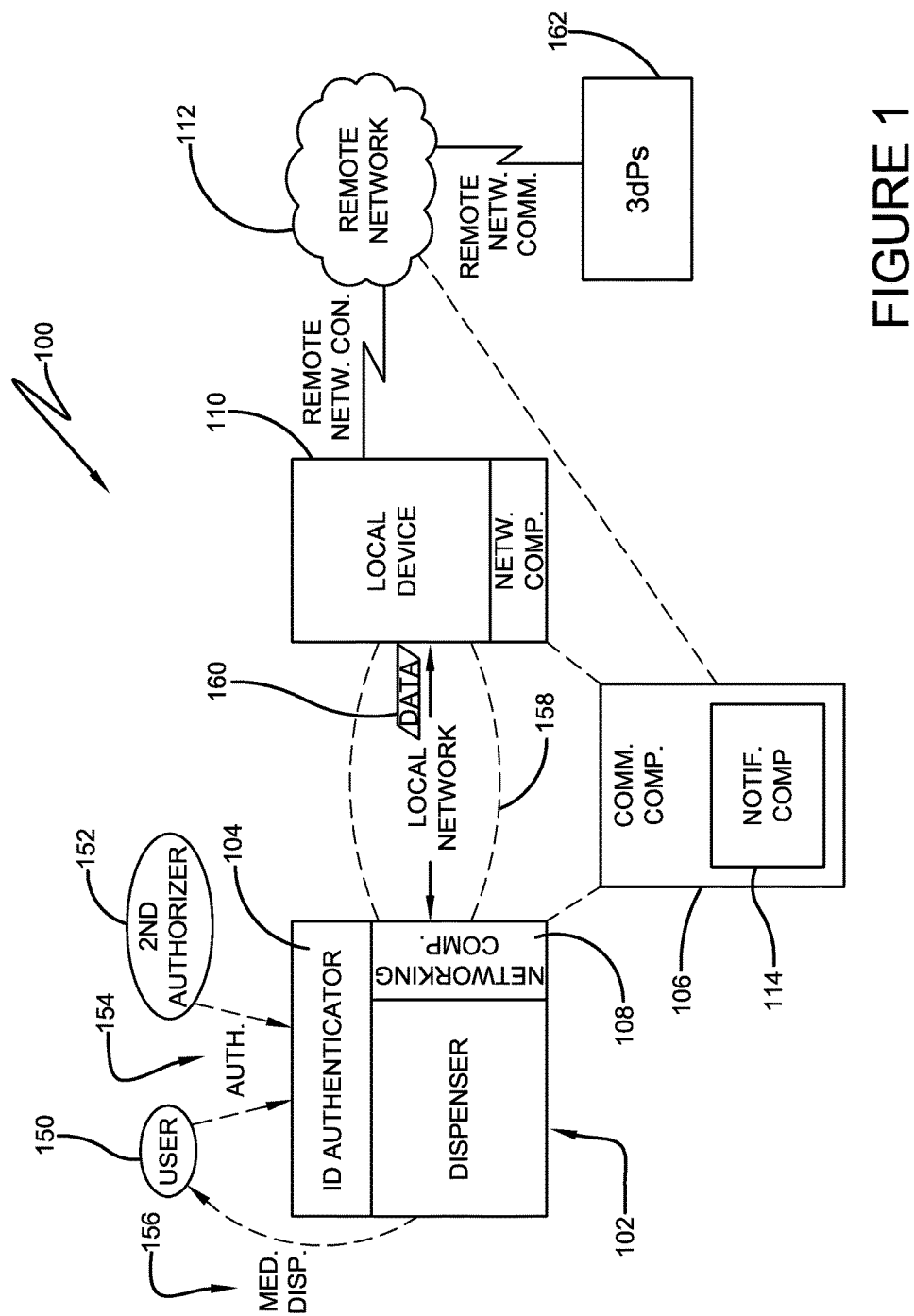
FIG. 1 is a schematic diagram illustrating an example implementation of an exemplary system for medicine dosage compliance.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices may be shown in block diagram form in order to facilitate describing the claimed subject matter.

In one aspect, a system may be devised that provides for appropriate dispensing of medication (e.g., prescribed behind the counter, or non-prescribed over the counter) to a user, along with notifications of dispensing to third parties associated with the user. In this way, for example, the user may be provided with improved medical care experience, and certain third parties can have the appropriate information used to provide the improved experience. In one implementation, a device used to hold and/or dispense medication may be opened to dispense the medication after proper authentication of a user and a secondary authenticator (e.g., authorized witness, or third, fourth, etc. authenticators). In this way, for example, the medication may merely be dispensed to the proper user at the proper time, and interested third parties can be notified when it occurs. It should be noted that such a system may also be used for dispensing of other substances not medically related, such as vitamins, supplements, supplies, non-food items, etc.

FIG. 1 is a schematic diagram illustrating an example implementation of a system 100 for medicine dosage compliance. The example system 100 comprises a dispensing component 102 that provides for medicine to be dispensed based at least upon authorized identification of a user 150 and a secondary authorizer 152. In this implementation, the dispensing component 102 comprises an identity authentication component 104 that can automatically authenticate 154 the identity of the user and the secondary authorizer, at the time of the intended dispensing event 156. As an example, the user may be alerted (e.g., automatically using an on-board alerting component, based on a medication schedule) that the user's medicine dose is scheduled to occur. In this example, after being alerted, the user can activate the identity authentication component to achieve user authentication. Further, a secondary authorizer, such as an authorized witness (e.g., and a third, fourth, etc., multiple authenticators), can activate the identity authentication component (e.g., prior to, concurrent with, or subsequent to the user) to achieve secondary authorizer authentication. Additionally, in this example, upon both user and secondary authorizer's authentication, the dispensing component may automatically provide access to the appropriate medicine dose (e.g., or provide the dose), resulting in the dispensing event (e.g., actual dispensing of a dose, and/or access the stored medicine).

As shown in FIG. 1, the example system 100 can comprise a communication component 106 that provides one or more notifications to one or more third parties. The communication component 106 comprises a wireless personal area networking component 108 that sets up a local networking connection 158 with a local device 110. The local networking connection 158 can be used to share data 160 between the dispensing component 102 and the local device 110. In this implementation, the local device 110 is communicatively coupled to a remote network component 112. Further, in this implementation, the communication component 106 comprises a notification component 114 that generates notification information 116 of the dispensing event for one or more third parties 162.

In one or more implementations, one or more portions of the communication component 106 may be disposed on, or operably coupled with, the dispensing component 102, the local device 110, and/or the remote network component 112. As an example, a portion of (e.g., or all of) the networking component 108 can be disposed on/in the dispensing component and the local device (e.g., a computing device, such as a smartphone, smart device, tablet, computer, etc.), such that a local area network (e.g., a short-range or nearfield communication network) can be established between the dispensing device 102 and the local device 110. As an example, the dispensing device 102 can comprise a Bluetooth module, and the local device can comprise a separate Bluetooth module, which can be used to create a local Bluetooth connection with each other, for data sharing. Further, for example, a portion of the notification component 114 can be disposed on the dispensing component 102, the local device 110, and/or the remote network component 112. In this example, data indicative of a dispensing event is communicated to the local device 110 from the dispensing component 102, and communicated to the remote network component 112 by the local device 110, which can generate notification information 116 of the dispensing event to one or more third parties 162, and/or store information relating to a dispensing event (e.g., or other notification/update information).

Figure 2A:
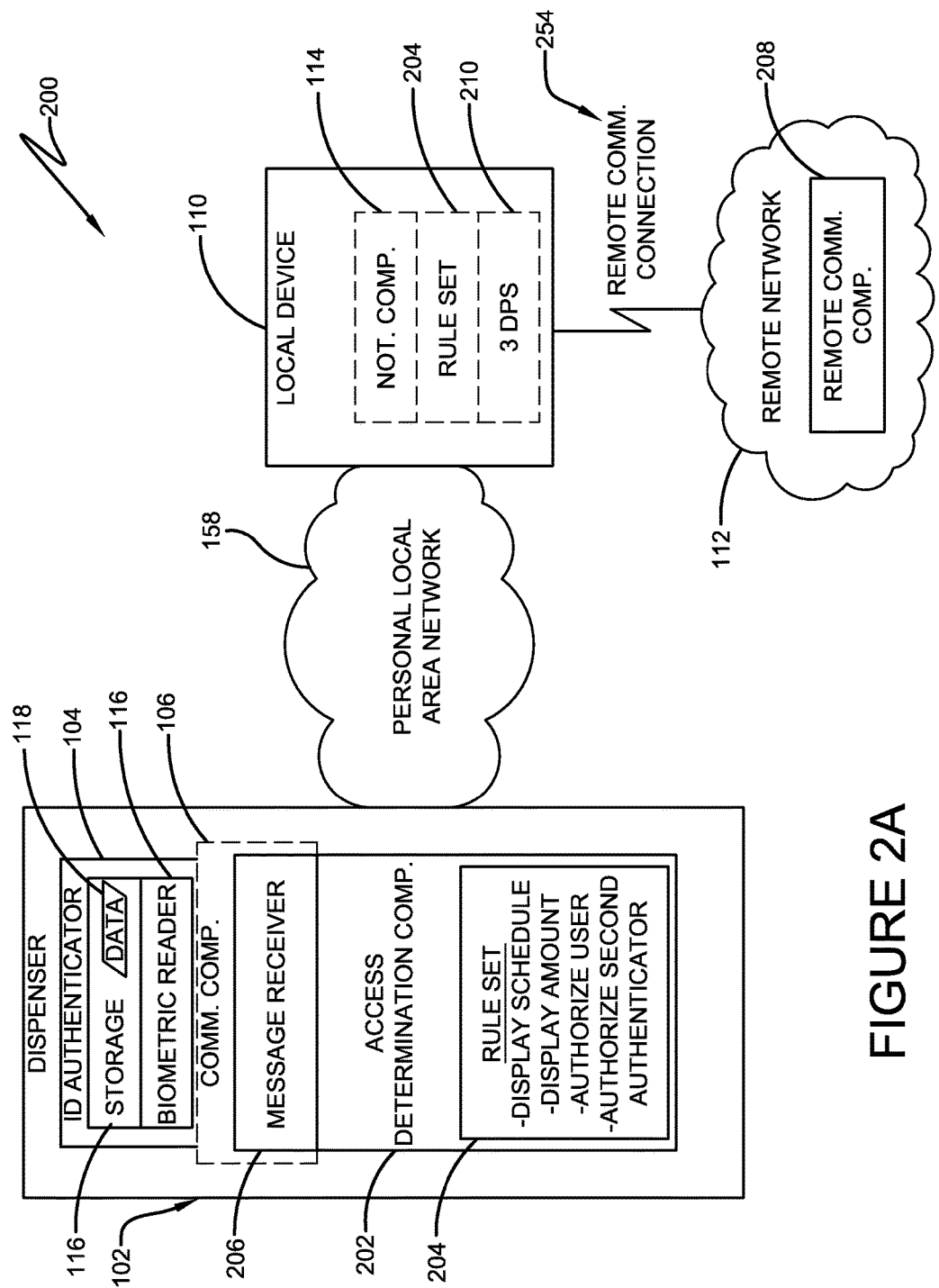
FIGS. 2A and 2B are schematic diagrams illustrating an example implementation of one or more portions of one or more systems described herein.
Figure 2B:
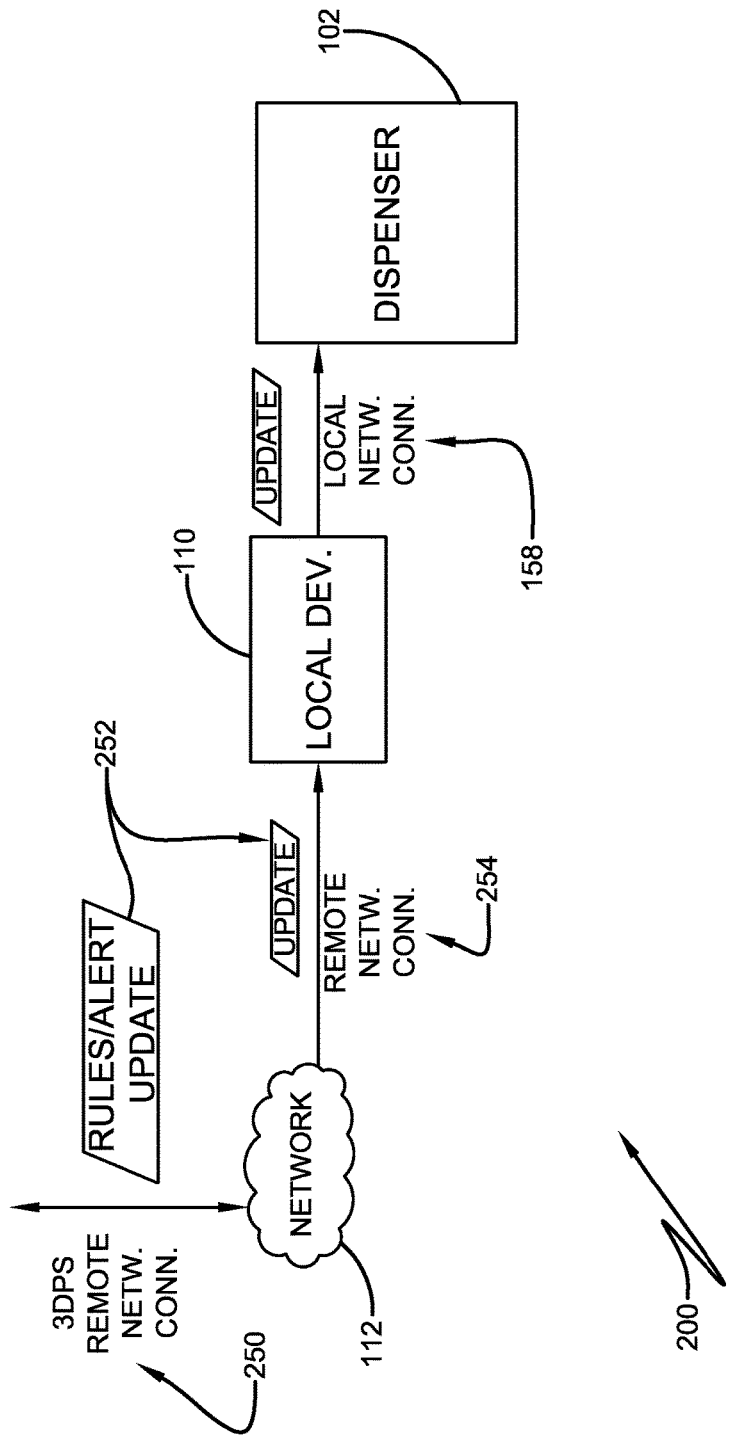

FIGS. 2A and 2B are schematic diagrams illustrating an example implementation 200 of one or more portions of one or more systems described herein. In one implementation, the dispensing component 102 can comprise an access determination component 202. The access determination component 202 can be configured to determine access authorization for dispensing the medicine stored in the dispensing component 102, based at least upon a rule set 204. That is, for example, a set of pre-determined rules can be used to determine whether the stored medicine should be dispensed. In this example, a processor associated with the access determination component 202 may compare data associated with the existing situation to the rules set 204, and, based on that comparison, determine whether the medicine should be dispensed.

In one implementation, the rule set 204 can comprise a dispensing schedule, which may include the desired date and time of dispensing, the type of medication dispensed, and other factors associated with prescribing a medical course that includes medication. Further, in one implementation, the rule set 204 can comprise a dispensing amount (e.g., which may be included in the dispensing schedule). That is, for example, the dispensing component 102 may provide for dispensing merely an amount prescribed (e.g., or instructed) at a particular time, over a period of time. Additionally, the rule set 204 can comprise information associated with an authorized user of the medicine, and/or information associated with an authorized secondary authenticator associated with the authorized user. That is, for example, the rule set 204 may be configured to allow merely one authorized user, according to the medical prescription (e.g., or other dispensing instructions). In this example, a secondary authenticator (e.g., or multiple authenticators) may be an authorized witness, or someone authorized to allow dispensing of the medication, and their information can also be comprised in the rule set 204. In one implementation, one or more portions of the rule set may be stored in storage located in the access determination component 202, and/or the local device 110 that is coupled with the dispensing component 102 in the wireless personal area network 158.

As an illustrative example, the rules set 204 may be comprised of information from a medical treatment plan for an authorized user, which includes information relating to a medicine schedule (e.g., dosage rate, time, refills, instructions, etc.). In this example, the authorized user may be subjected to specific requirements that necessitate the use of a secondary authenticator for the purpose of authorizing dosage, and/or witnessing dosage (e.g., in a primary school situation involving a student and a school clinician). At the prescribed or instructed time (e.g., as alerted by an on-board alerting system), the authorized user may provide their identification to the dispensing component 102, and the secondary authenticator may also provide their identification. In this example, the access determination component 202 (e.g., which may be linked to the identification authenticator 104) can compare the user and secondary authenticator's IDs to the rule set, the time of proposed access to the rules set, any previous dosing events to current dosing requirements, and/or other potential information, to determine whether to dispense (e.g., or allow dispensing of) the medication.

In one implementation, as illustrated in FIGS. 2A and B, the communications component 106 can comprise a message receiving component 206. In this implementation, the message receiving component 206 can be configured to receive updates to the rule set 204, and/or receive alerts that are targeted to the user or the secondary authorizer. For example, as illustrated in FIG. 2B, with continued reference to FIG. 2A, data indicative of an update 252, such as a rules set update or an alert update, may be provided by a third party through a remote third party connection 250 to the remote network 112.

As an example, the remote network may comprise, or be connected with, a remote communication component 208, which may be a portion of the communication component 206. In this example, the remote communication component 208 can be configured to provide updates 250 to the rule set 204, and/or user alerts, which may originate from a third party associated with the user (e.g., pharmacy, physician, caretaker, other sources). Further, in this example, the update can proliferate to the local device 110 through its remote connection 254 with the remote network 112, and to the message receiver 206 engaged with the dispensing component 102 through the local area network 158. In this way, for example, the update 252 to the rules set 204 may be used to create an updated rule set, which may alter the way the access determination component 202 provides access to the medicine in the dispensing component 102.

Alternately, in one implementation, the updated alert 252 can be provided to the user or secondary authenticator (e.g., and/or pre-determined third parties), such as using an alerting component (e.g., display). As one example, the dispensing component 102 can comprise an alerting component configured to provide feedback to the user (e.g., and secondary authenticator, or others associated with the user). An alerting component may comprise some sort of visual display and/or auditory component that provides information to the user. A visual display can comprise one or more lights (e.g., color changing, or multiple colors, such as red and green), or a display component that provides messages to the user, for example. Additionally, the alerting component can comprise an auditory component that provides auditory signals (e.g., beeps or tones), or voice messages to the user, for example. In one implementation, the alerting component can be used to provide and indication to the user, secondary authenticator or others, that proper or improper authentication has been provided. For example, a red light may be indicated for improper authentication (e.g., or improper sequence), and a green light may be indicated for proper authentication.

There may be occasions when the local area network 158, and/or the remote network 112 may not be available (e.g., local device not present, trouble connecting, no connection available, etc.). In one implementation, the information regarding a dispensing event (e.g., or some alert, update, etc.) may be stored locally, such as in storage disposed in the dispensing component 102, and/or the local device 110. In this implementation, for example, when the local area network 158, and/or the remote network 112 become available, a syncing event may occur that allows data indicative of the dispensing event to be received by the remote network 112; or information from the remote network 112 can be synced with the local device 110, and/or the dispensing component 102.

In one implementation, the update 252 received by the message receiving component 206 can comprise authorization from a primary authorizer, where the authorization from the primary authorizer comprises authorizing access to the dispensing component 102 to dispense medicine. That is, for example, a primary authorizer may comprise a primary caregiver, such as a parent or guardian responsible for the user. In this example, the medicine in the dispensing component 102 may merely be accessed upon receiving authorization from the primary authorizer (e.g., followed by ID authentication of the user and secondary authenticator). As an illustrative example, the user may be a student at school that takes medication on a prescribed or instructed schedule, and the secondary authenticator may be the school's clinician. In this example, the student's guardian can send authorization from a third party computing device, through the remote communication component 208, over the remote network 112, to the local device 110. Further, in this example, the local device 110 (e.g., clinician's phone, computer, tablet; or student's phone table, etc.) can communicate the primary authorization to the dispensing device; thereby allowing the access steps to be taken (e.g., according to the rules set 204).

With continued reference to FIGS. 1, 2A and 2B, in one implementation, the communication component 106 can comprise the local device 110 that is communicatively coupled to the remote network 112. In this implementation, the local device 110 can comprise at least a portion of the notification component 114, and a predetermined list of third parties 210 to which the data indicative of one or more notifications 160 are sent. For example, as described above, one or more portions of the notification component 114 can be disposed on one or more portions of the system 100, including the dispensing component 102, the local device 110, and/or the remote network 112 (e.g., including the remote communications component 208). In this example, a portion of the notification component 114 is disposed in the local device 110 (e.g., as a combination of programming and hardware), and, using the list of third parties 210, can provide the notifications (e.g., dispensing events) to those listed third parties (e.g., using the remote network 112).

In one implementation, the one or more notifications (e.g., data indicative of notifications 160) can comprise a notification to a primary authorizer that the dispensing component 102 was accessed and/or re-secured after access, for example, comprising a dispensing event. In this way, for example, the primary caregiver or guardian can receive a notice (e.g., via a smart device, or other computing device) that the user accessed the dispensing component 102 to receive a dose of the medicine. In one implementation, the one or more notifications can comprise a notification to a predetermined clinician that the dispensing event has occurred; a notification to a predetermined pharmacy that the dispensing event has occurred; a notification to a predetermined pharmacy of an expected amount of medicine remaining after the dispensing event has occurred; and/or a notification to a predetermined third party that the dispensing event has occurred. For example, those third parties that may have an interest in identifying when a user receives a dose can be notified. In one example, the pharmacy may receive notice of an amount of medicine left in order to provide for an appropriate refill, notify the physician of the need for a new prescription, and/or notify the user of the potential end of the dosage. Additionally, a notification may be provided to the user that the dispensing component 102 was accessed and/or re-secured after access, for example, which may include access occurrences that were unauthorized or authorized.

In one implementation, the one or more notifications can comprise a notification to a predetermined health care insurer that the dispensing event has occurred; and/or a notification to a predetermined electronic medical record that the dispensing event has occurred. As an example, other third parties may have a vested interest in determining whether or not the user is following the prescribed course of medical action, including medicine use. An insurance company may be interested in order to provide improved insurance rates to the user or user's group. Further, a user's electronic medical record (EMR) can be automatically updated by the notifications, which may allow users of the EMR to be updated accordingly. For example, a dispensing event can be populated to the user's EMR automatically using a notification.

In one implementation, the notification component 114 can be configured to provide a notification to one or more of the third parties 162, the user, or others, of an unauthorized access attempt. As an example, if an unauthorized person attempts to access the dispensing component 102, such as by providing their unauthorized identification, and/or attempting to physically access the dispensing component 102 without authorization, a notification can be provided to one or more of the third parties 162 (e.g., and others) indicating the attempted access. As another example, if access is attempted that is not in compliance with the rules set (e.g., wrong time, wrong authenticator, etc.), the notification of an attempt can be provided.

In one implementation, the secondary authenticator (e.g., or another third party) can act as a witness, and may be present during a dispensing event. In this implementation, the witness can positively identify that the user consumed the appropriate dispensed medicine (e.g., visual identification). Further, the witness may provide authentication (e.g., using the biometric scanner) that the user consumed the medicine, and data indicative of the provided authentication can be automatically transmitted to the local device 110. In this implementation, the data indicative of the authentication of consumption can be transmitted to the remote network 112, and a notification of the authentication of consumption can be provided to one or more of the associated third parties (e.g., clinician, health care provider, EMR, caregiver, etc., and/or primary authorizer).

In one implementation, the identity authentication component 104 can comprise a biometric reader that captures a biometric marker of the user and/or the secondary authorizer. Further, in one implementation, the identity authentication component 104 can comprise data storage 116 that stores authentication data 118 associated with at least the user and the secondary authorizer. As an example, the authentication data 118 stored in the data storage 116 may comprise biometric markers for the user and the secondary authenticator, which may have been pre-enrolled and stored in the data storage 116. In this example, the user and/or the secondary authenticator may use the biometric reader 116 (e.g., fingerprint reader, or any other biometric reader) to enter their identification. In this example, the biometric markers read by the reader 116 can be compared with the stored biometric data 104, such as using a processor linked with the identification authentication component 104, to determine if the entered biometric markers match those of the user and/or the secondary authenticator (e.g., or other authenticators). In this way, for example, access may be provided to the dispensing component 102, at least in part, by using the biometric reader 116.

Figure 3:
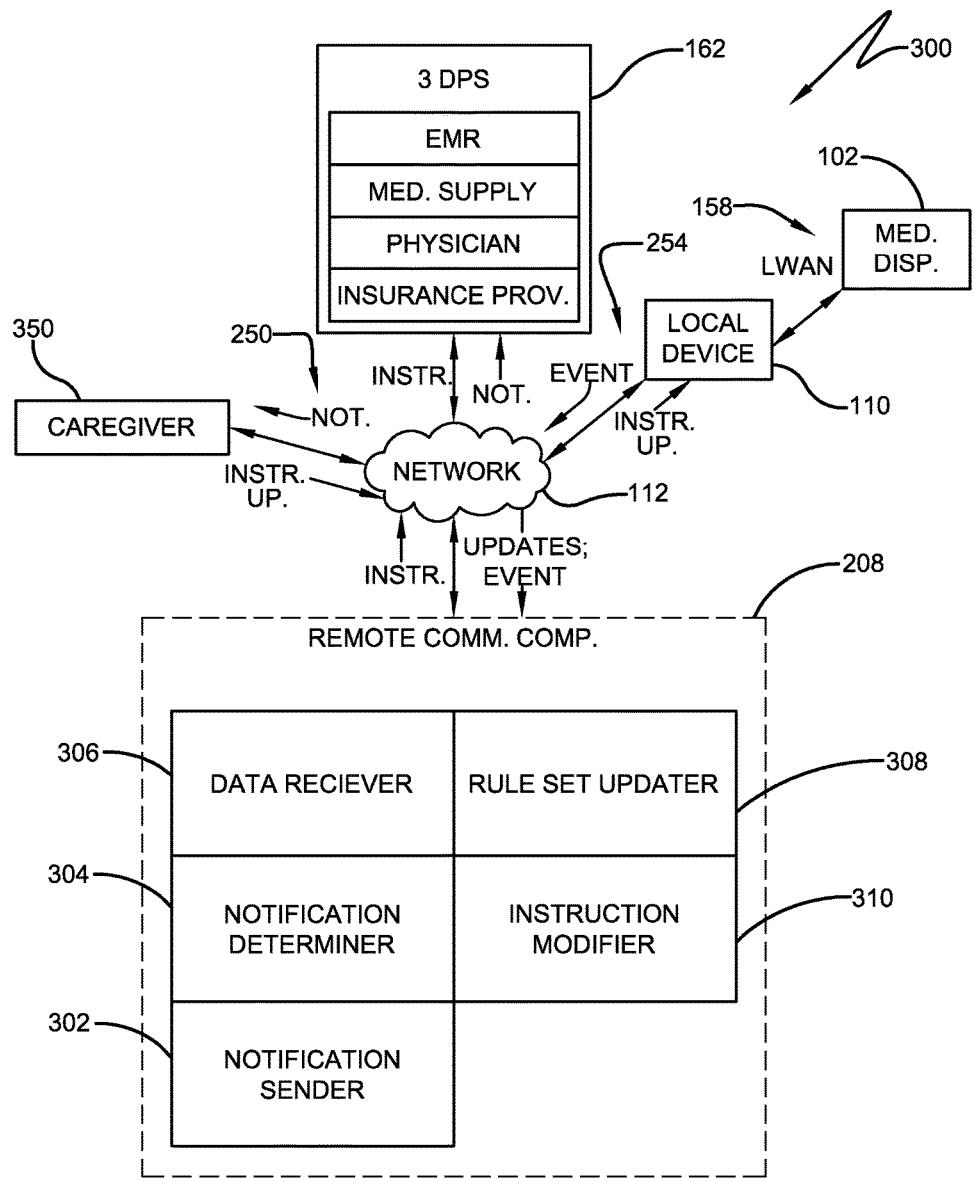
FIG. 3 is a schematic diagram illustrating an example implementation of an exemplary environment where of one or more portions of one or more systems described herein may be implemented.
Figure 4A:
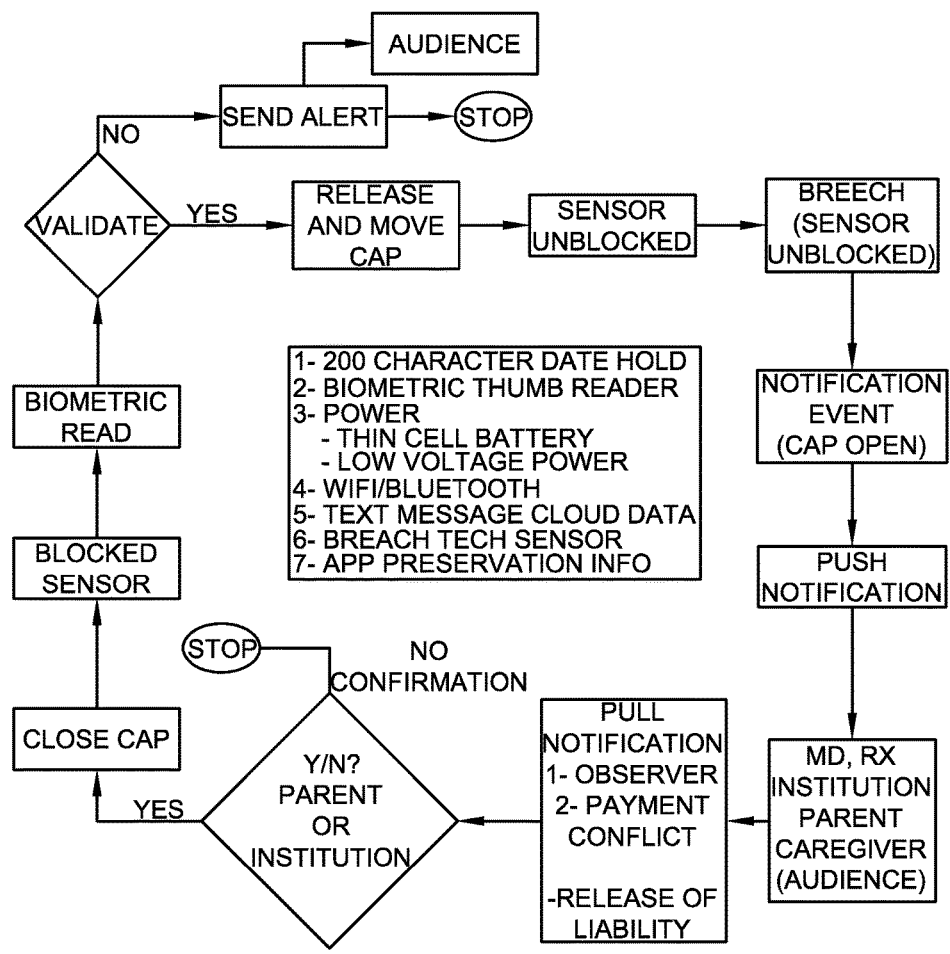
FIGS. 4A and 4B are schematic diagrams illustrating an example implementation of one or more portions of one or more systems described herein.
Figure 4B:
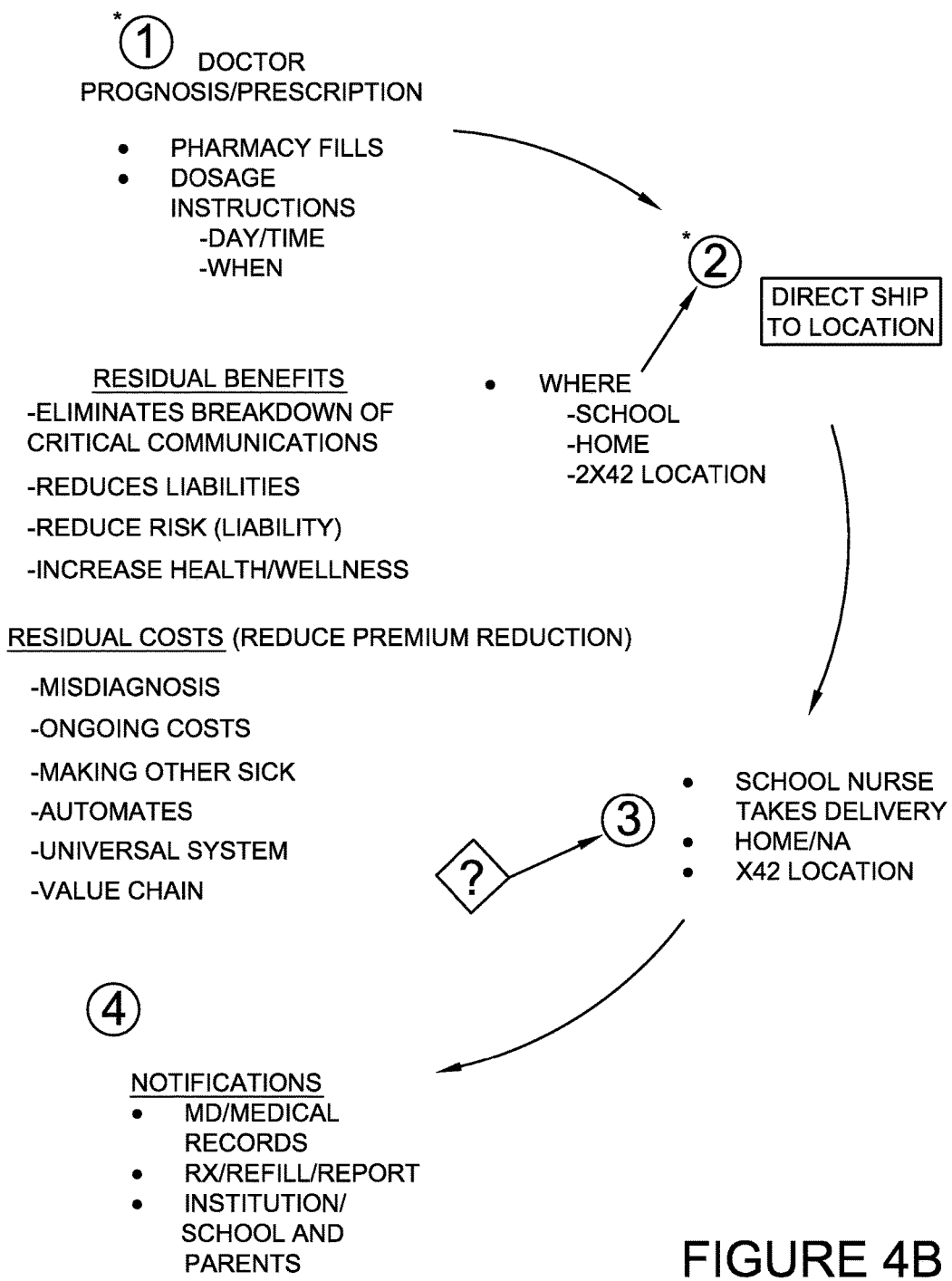
Figure 6:
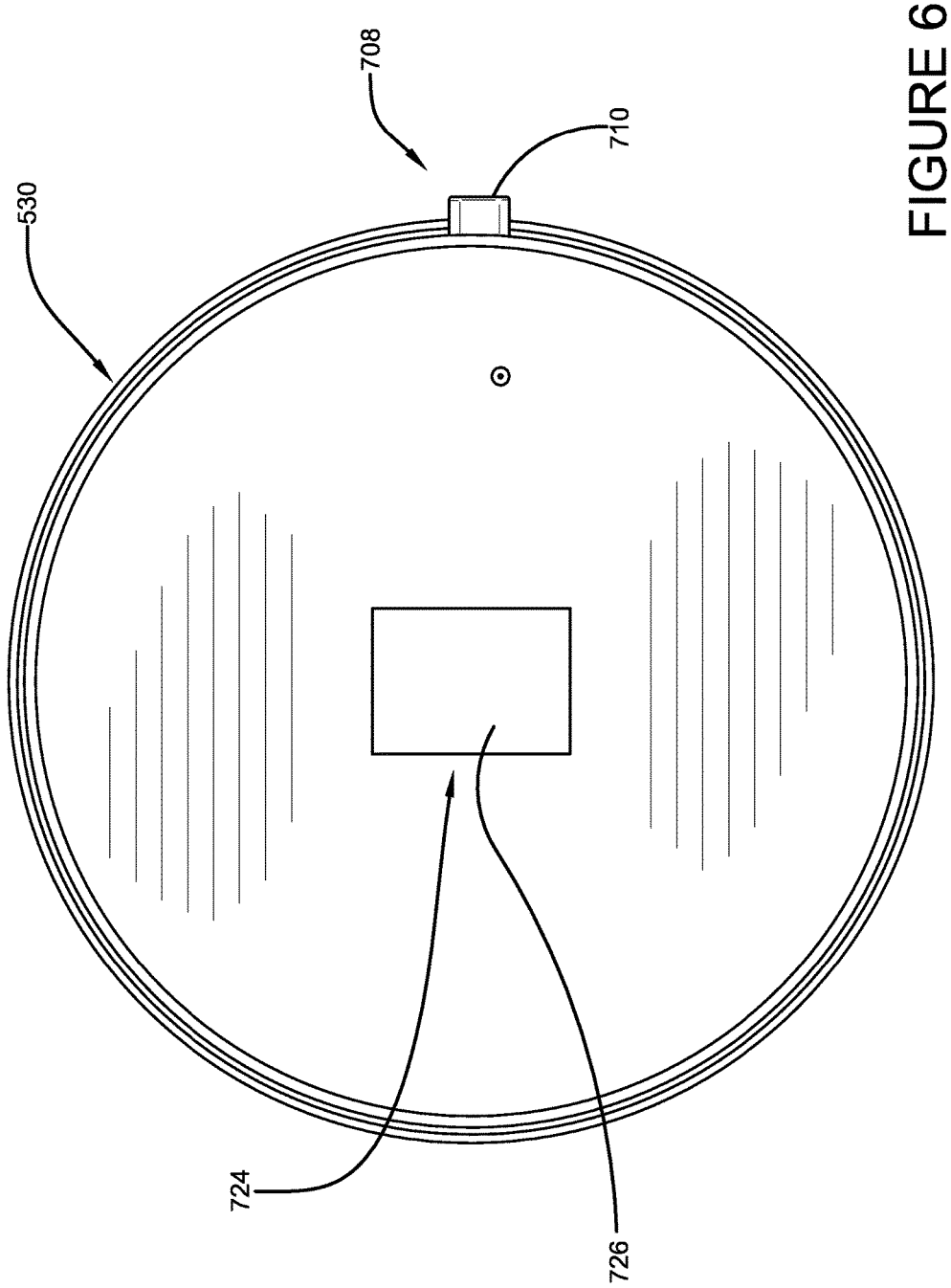
FIG. 6 is a top view of one or more portions of one or more systems shown in FIG. 5.

FIG. 3 is a schematic diagram illustrating an example environment 300 where one or more portions of one or more systems described herein may be utilized. With continued reference to one or more elements from FIGS. 1, 2A and 2B, in this example environment 300, the dispensing component 102 can be communicatively coupled with the local device 110 using the local network 158. Further, the local device 110 can be communicatively coupled with the remote network 112 using a remote network connection 254. Additionally, the one or more third parties 162, which can include the primary caregiver 350 (e.g., guardian), may be communicatively coupled with the remote network 112 using one or more separate remote communication connections 250. As shown in the example environment 300, the one or more third parties 162 (e.g., connected separately or though a shared connection) can comprise the EMR, medicine supplier (e.g., pharmacy), physician or primary health care provider, and/or the insurance provider group.

In this example implantation 300, the remote network 112 may be coupled with (e.g., or may comprise) the remote communication component 208. As an example, the remote communication component 208 can comprise one or more computing devices (e.g., servers, data storage and manipulation services, cloud services, etc.) that are linked with or a part of the remote network 112. In this implementation, the remote communication component 208 can comprise a notification transmitting component 302 that automatically transmits data indicative of a notification 160 of the dispensing event to the one or more third parties 162, 350 associated with the user.

In one implementation, the remote communication component 208 can comprise a notification determination component 304 that determines which one or more of the one or more third parties 162, 350 are to receive the notification 160, based at least on the dispensing event. That is, for example, depending on the type of dispensing event, not all of the 3 dPs may receive the notification. As an example, the primary caregiver 350 may receive all notifications, but the other 3 dPs 162 may merely receive periodic updates, as needed (e.g., refills, finished medical course, missed dose, etc.). In one implementation, the remote communication component 208 can comprise an update receiving component 306 that receives data indicative of the dispensing event 160, and/or data indicative of a dispensing rule set instructions update (e.g., from a primary care provider and/or pharmacy). As an example, the dispensing event can comprise opening of a secured medicine container; securing of a medicine container; request for access to a medicine container; attempted unauthorized access to a secured medicine container; security breach of a secured medicine container; and/or a missed dosage event for the user.

Further for example, updates to the rule set 204, can comprise updates to one or more of: data indicative of an identification of the user; data indicative of an identification of the secondary authenticator (e.g., or multiple authenticators); biometric data indicative of the identification of the user; biometric data indicative of the identification of the secondary authenticator; data indicative of a dosage schedule for the user of the medicine; and/or data indicative of an authentication procedure for accessing the secured medicine.

In one implementation, the remote communication component 208 can comprise a rules set modification component 310 that determines an update to the dispensing rules set 204. The update to the rules set 204 can be based upon rule set updating instructions received from a third party 162, and/or data from the one or more dispensing events. In this implementation, the update receiving component 306 can provide the information to the rule set modification component 310. As an example, updates to the rule set 204, can comprise updates to one or more of: data indicative of an identification of the user; data indicative of an identification of the secondary authenticator; biometric data indicative of the identification of the user; biometric data indicative of the identification of the secondary authenticator; data indicative of a dosage schedule for the user of the medicine; and/or data indicative of an authentication procedure for accessing the secured medicine.

The remote communication component 208 can comprise a rules set updating component 308 that transmits an update to the dispensing rule set to the local device 110 using the remote coupling 254 with the local device 110. As an example, the updated rules set information can be communicated to the message receiving component 206, and used to update the rules set 204 in the access determination component 202.

In one implementation, the remote communication component 208 can comprise a data storage component that is configured to store data indicative of a dispensing event, a notification, authorization information, and/or update information. As an example, information relating to respective dispensing events can be stored remotely on the remote communication component 208, such as for later review and analysis, transmitting to appropriate parties (e.g., upon reconnection of the network), and/or record keeping. Further, as an example, notifications can be stored remotely and disturbed to appropriate third parties at pre-determined times/intervals. Additionally, prescription, instruction, or authorization update information may be stored remotely, and transmitted to the dispensing component 102 at pre-determined times, or upon connection to the remote network (e.g., through the local device 110).

With continuing reference to FIGS. 5-10, one nonlimiting implementation of the dispensing container 102 and closure component 505 may be a container 500. The container may have a body 510, which may take a variety of forms including without limitation bottles, pill containers, jars, vials, liquid containers, or medicine bottles. The closure component 505 may have several implementations including without limitation, caps, droppers or other secure covering.

In one nonlimiting implementation, the body 510 may take the form of a bottle 512. The bottle 512 may have a bottom 514 and at least one side wall 516 operably connected thereto. In one implementation, the side wall 516 may have a curvature so as to form a cylinder with the bottom 514. However, any shape chosen with sound engineering judgment may be utilized, including without limitation, round, square, rectangular, oval or other shape. The bottom 514 and the side wall 516 may define at least a partial cavity 518 therein. The cavity 518 may extend any distance into the body to form a partial cavity or a full cavity. The cavity 518 may receive any variety of objects 520 for storage. By way of nonlimiting example, the objects 520 may be medicine (e.g. pills or liquid) 522, or nonmedicinal such as nails used for construction projects, money (e.g., bills or coins), and jewelry. The objects 520 may be anything that may fit within the cavity 518 and may need restricted access. The bottle 512 may also comprise a top portion 524. The top portion 524 may have a lip 526, a groove (not shown), threads 528 or other mechanism for receiving the closure component 505. The bottle 512 may be formed from any material chosen with sound engineering judgment. In the implementation of medicine, the bottle 512 may be formed of glass, polypropylene, resin, polyethylene terephthalate, high-density polyethylene or other plastic. For nonmedicinal objects 520, materials may include glass, plastic, polymer or any other material chosen with sound engineering judgment.

In one nonlimiting implementation, the top portion 524 of the bottle 512 may be configured to receive the closure component 505. In one nonlimiting implementation, the closure component 505 may be a cap 530. The cap 530 may also be lockable relative to the bottle 512. The cap 530 may have a top surface 532 and a side wall 534 extending therefrom. In one implementation, the side wall 534 may have a curvature so as to form a cylinder with the top surface 532. However, any shape chosen with sound engineering judgment may be utilized, including without limitation, round, square, rectangular, oval or other shape. The top surface 532 and the side wall 534 may define at least a partial cavity 536 therein. The cap cavity 536 may extend any distance into the cap to form a partial cavity or a full cavity. The side wall 434 may have a bottom portion 538. The bottom portion 538 may have the same diameter D1 as the top surface 532 or it may be a second diameter D2, which may be larger than D1. The bottom portion 538 may have lip 540, a groove (not shown), threads 528 or other mechanism for securely attaching to the bottle 512. The cap side wall 534 may further comprise a power switch 542 to energize or de-energize components of the cap 530 to be described in further detail below.

Figure 7A:
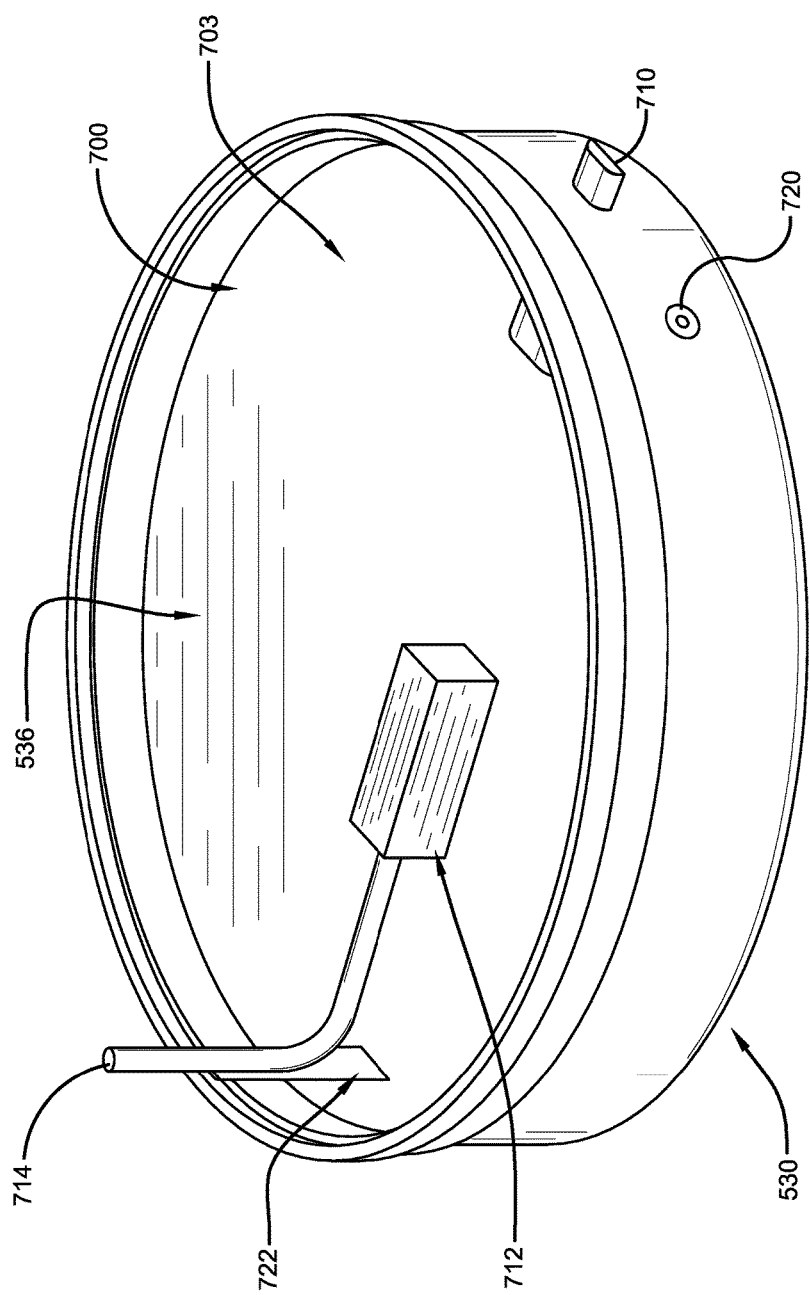
FIG. 7A is a bottom perspective view of one or more portions of one or more systems shown in FIG. 5.
Figure 7B:
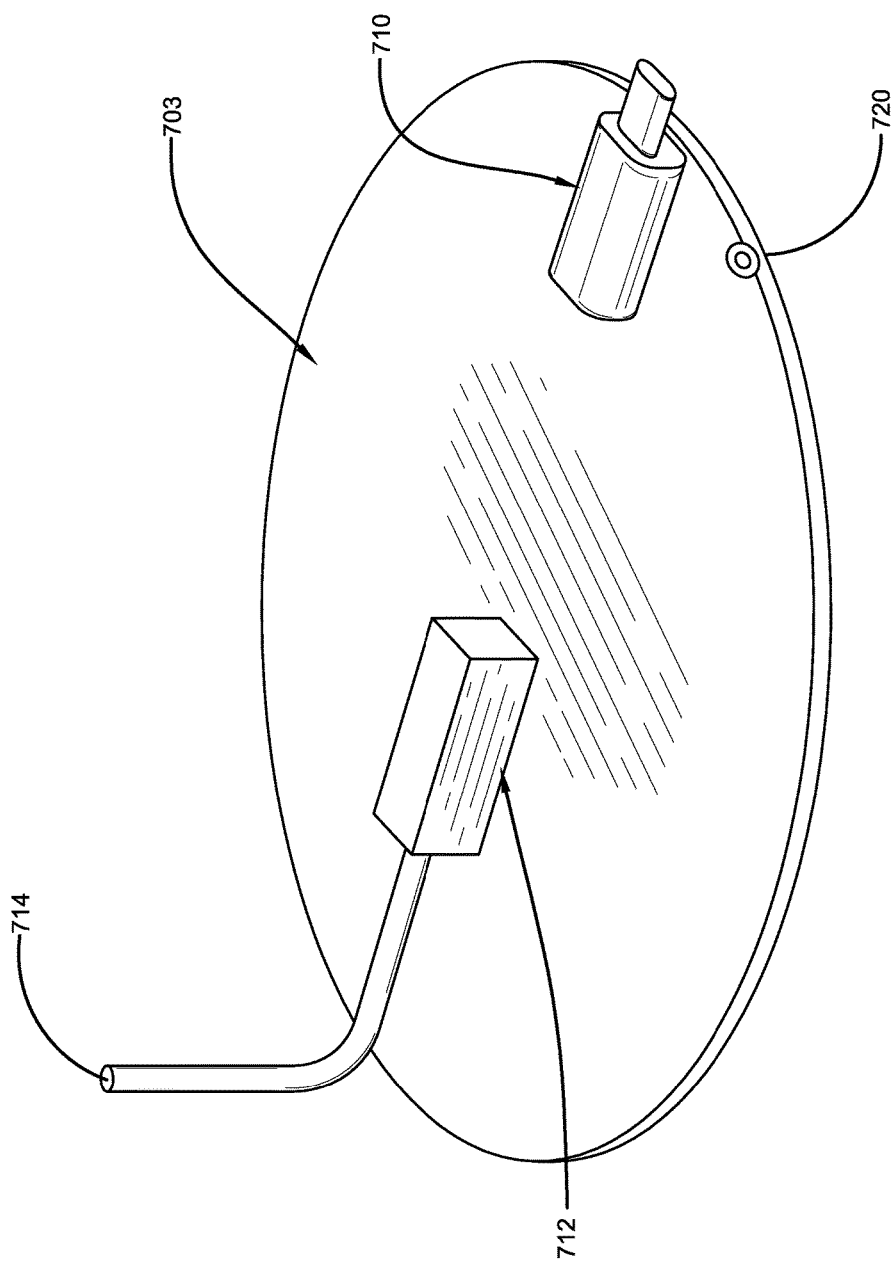
FIG. 7B is a bottom perspective view of one aspect of one or more portions of one or more systems shown in FIG. 7A.
Figure 7C:
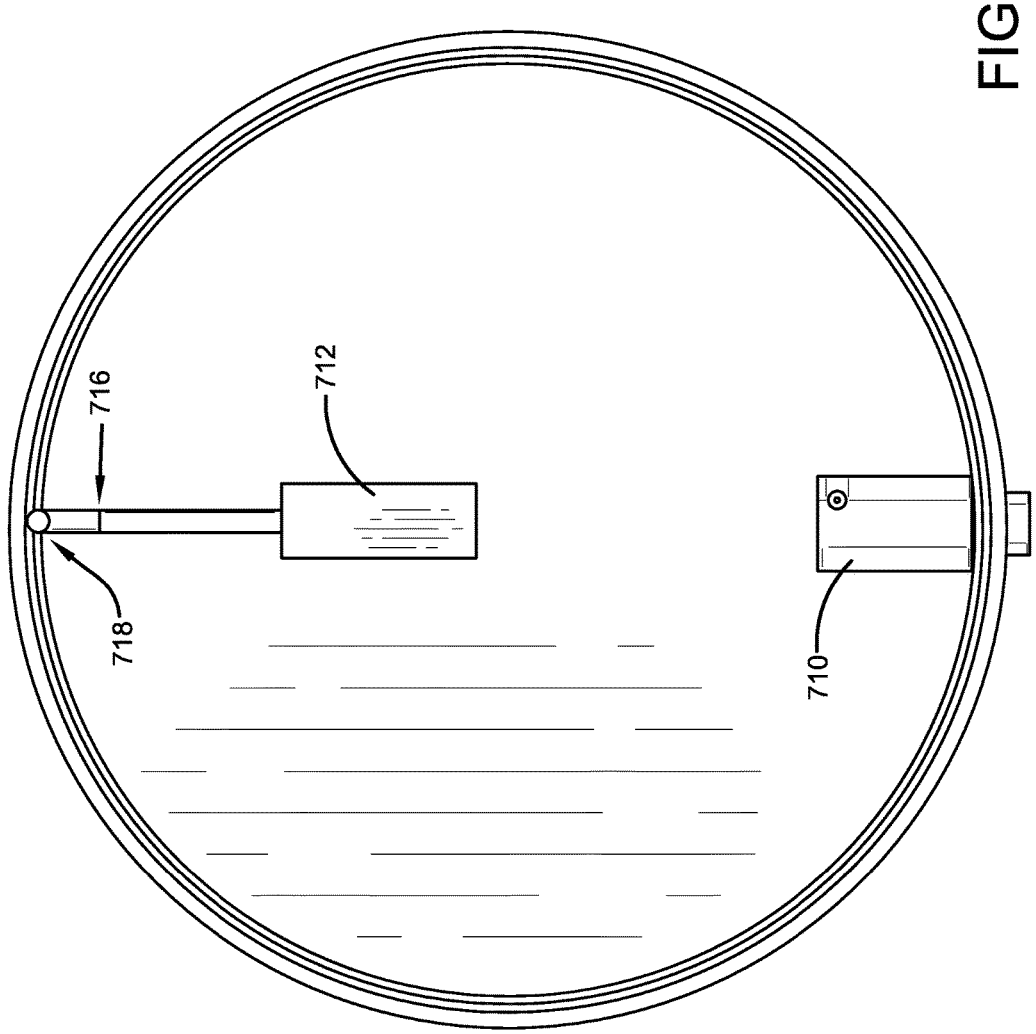
FIG. 7C is another bottom view of one or more portions of one or more systems shown in FIG. 7A.

With reference to FIGS. 7a-7c, the cap has a base surface 700 which is oppositely disposed from the top surface 532. The base surface may comprise a variety of components to lock the cap 530 to the bottle 512. The base surface may have a printed circuit card 703 disposed thereon. The printed circuit card may have a battery 704 for supplying energy to a power source 702. The battery may take any form chosen with sound engineering judgment, and in one implementation may be a lithium-ion polymer battery. The battery 704 may also be a lithium CR2032 coin cell battery. The battery 704 may be rechargeable. The battery 704 may be recharged with a recharging unit 708. The recharging unit 708 may be operably connected with the cap 530, or the recharging unit 708 may be positioned separately from the cap 530 and bottle 512. In one nonlimiting implementation, the recharging unit 708 may be a USB charging port 710. The USB charging port 710 may receive the appropriate USB connector (not shown), which attaches to an adapter for power or another device, for example, a computer.

The printed circuit card 703 may comprise the power source 702. In one implementation, the power source 702 may be a servo motor 712. The servo motor 712 is small, such as one used in the drone industry. The servo motor 712 acts as a linear actuator to push a locking pin 714 from a first position 716 to a second position 718. The locking pin 714 is normally in a locked first position 716. Upon activation of the servo motor, the servo motor pushed the locking pin 714 to the second position 718, which is unlocked. When the locking pin 714 is in the unlocked second position 718, the locking pin pushes against the cap sidewall 534. The cap sidewall 534 is moved past a blocking element 550, which may be disposed on the bottle 512. Once the cap side wall 534 moves past the blocking element 550, the cap 530 may be removed from the bottle 512. In another implementation, the locking pin 714 may place pressure against a cap detent 722, which moves to a position away from a blocking element (not shown) so that the cap 530 may be removed.

In another aspect of the present invention, the cap 530 may have an alignment sensor 720. The alignment sensor 720 is utilized to ensure the cap 530 remains locked. Upon an attempted unauthorized access attempt to the bottle 512, the alignment sensor will send a signal, by way of example through an alert message, indicating position misalignment. Likewise, if the cap 530 is opened with proper authorization, the alignment sensor will not trigger an alert upon removal of the cap 530.

With continued reference to FIGS. 5-7c, the cap 530 may further comprise an identify authentication component 724 and an access determination component 726. The identity authentication component 724 may be configured to verify the identification of the user, the primary authorizer or the secondary authorizer. In one implementation, the identity authentication component 724 may be a biometric reader 726 that may be able to capture characteristics such as fingerprints, iris scans, retinal scans, ear, facial recognition, finger geometry, hand, voice, and other physical characteristics. In one implementation, the biometric reader 726 may be configured to read fingerprints of the user, the primary authorizer or the secondary authorizer. The access determination component 727 may be a storage device 728. The storage device may be a memory chip or other device configured to store biometric information. In one implementation, the storage device 728 may be able to save and store up to ten records. In another implementation, the storage device 728 may be able to save and store up to twenty records. A record may include biometric data of a user, primary authorizer or the secondary authorizer. The record may also include events showing times that bottle 512 and cap 530 are opened or any combination thereof.

With reference to FIGS. 8A-8F, another implementation of the present invention is shown and described. A cap 830 may have a base surface 800 which is oppositely disposed from a top surface 832. The base surface 800 may comprise a variety of components to lock the cap 830 to the bottle 512. In an alternative implementation, the base surface 800 may have a plate member 803 disposed thereon for having various components operably attached thereto. The plate member 803 may have a battery 804 for supplying energy to a power source 802. The battery may take any form chosen with sound engineering judgment, and in one implementation may be a lithium-ion polymer battery. The battery 804 may also be a lithium CR2032 coin cell battery. The battery 804 may be rechargeable. The battery 804 may be recharged with a recharging unit 808. The recharging unit 808 may be operably connected with the cap 830, or the recharging unit 808 may be positioned separately from the cap 830 and bottle 512. In one nonlimiting implementation, the recharging unit 808 may be a USB charging port 810. The USB charging port 810 may receive the appropriate USB connector (not shown), which attaches to an adapter for power or another device, for example, a computer.

The plate member 803 may have the power source 802 operatively connected thereto. In one implementation, the power source 802 may comprise a servo motor 812. The servo motor 812 is small, such as one used in the drone industry. The servo motor 812 acts as a linear actuator to push a locking pin 814 from a first position to a second position. The change in position may be linear, rotational or a combination of both linear and rotational movement. In another implementation, the servo motor 812 may rotate the locking pin 814 from a first position 816 to a second position 818. The locking pin 814 may be normally in a locked first position 816. Upon activation of the servo motor, the servo motor may push the locking pin 814 to the second position 818, which is unlocked. When the locking pin 814 is in the unlocked second position 818, the locking pin may push against a cap sidewall 834. The cap sidewall 834 may move past a blocking element 550, which may be disposed on the bottle 512. In another implementation, the blocking element may be disposed within the cap 830. Once the cap side wall 834 moves past the blocking element 850, the cap 830 may be removed from the bottle 512. In another implementation, the locking pin 814 may place pressure against a cap detent 822, which moves to a position away from a blocking element (not shown) so that the cap 830 may be removed.

In another aspect of the present invention, the cap 830 may have an alignment sensor 820. The alignment sensor 820 is utilized to ensure the cap 830 remains locked. Upon an attempted unauthorized access attempt to the bottle 512, the alignment sensor will send a signal, by way of example through an alert message, indicating position misalignment. Likewise, if the cap 830 is opened with proper authorization, the alignment sensor will not trigger an alert upon removal of the cap 830.

With continued reference to FIGS. 8A-8F, the cap 830 may further comprise an identify authentication component 824 and an access determination component 826. The identity authentication component 824 may be configured to verify the identification of the user, the primary authorizer or the secondary authorizer. In one implementation, the identity authentication component 824 may be a biometric reader 826 that may be able to capture characteristics such as fingerprints, iris scans, retinal scans, ear, facial recognition, finger geometry, hand, voice, and other physical characteristics. In one implementation, the biometric reader 827 may be configured to read fingerprints of the user, the primary authorizer or the secondary authorizer. The access determination component 826 may be a storage device 828. The storage device may be a memory chip or other device configured to store biometric information. In one implementation, the storage device 828 may be able to save and store up to ten records. In another implementation, the storage device 828 may be able to save and store up to twenty records. A record may include biometric data of a user, primary authorizer or the secondary authorizer. The record may also include events showing times that bottle 512 and cap 830 are opened or any combination thereof.

In one implementation, the user may move the power switch 542, 842 to the on position in order to power the system. The battery 704, 804 may energize the system. The user or primary authorizer may place a finger on the biometric reader 727, 827. The biometric reader may compare the image to the authentication component 724, 824. An alert may be sent to a remote device to indicate the user desires to open the container 500 or have material (such as medicine) dispensed. A secondary authorizer may then place his or her finger on the biometric reader 727, 827 for authentication. If the authentication component 724, 824 verifies that material should be dispensed, and the user and authorizers are verified, the servo motor 712, 812 (or other power source) may actuate a locking pin 714, 814 to push against the closure component 505 and unlock the container 500. Then one of the authorizers may dispense the material (such as medication) to the user (such as a patient) and witness the user taking the material. Data is then sent to the remote device and other users, including an EMR, to document the event. It should be understood that any arrangement of components and parts may be undertaken to unlock the container in order to reach the objects 520 disposed therein.

In another implementation, the plate member 803 may have a mother board 830 and processor 832 attached thereto. The storage device 828 may be operably connected to the motherboard 830. Further, the USB charging port 810 may also be operably connected to the motherboard 830.

In another implementation of the present invention, a protective cover 835 may be operably attached to the cap 830 to prevent objects 520 from coming into contact with the components disposed in the lockable cap 530, 830. The protective cover 834 diameter may be coextensive with the diameter of the cap 530, 830. The protective cover 834 may be secured to the cap 530, 830 with fasteners or alternatively, press fit. A hole 836 may be defined through the protective cover 834 to enable the locking pin 714, 814 to be positioned for locking and unlocking the cap 530, 830.

Figure 9:
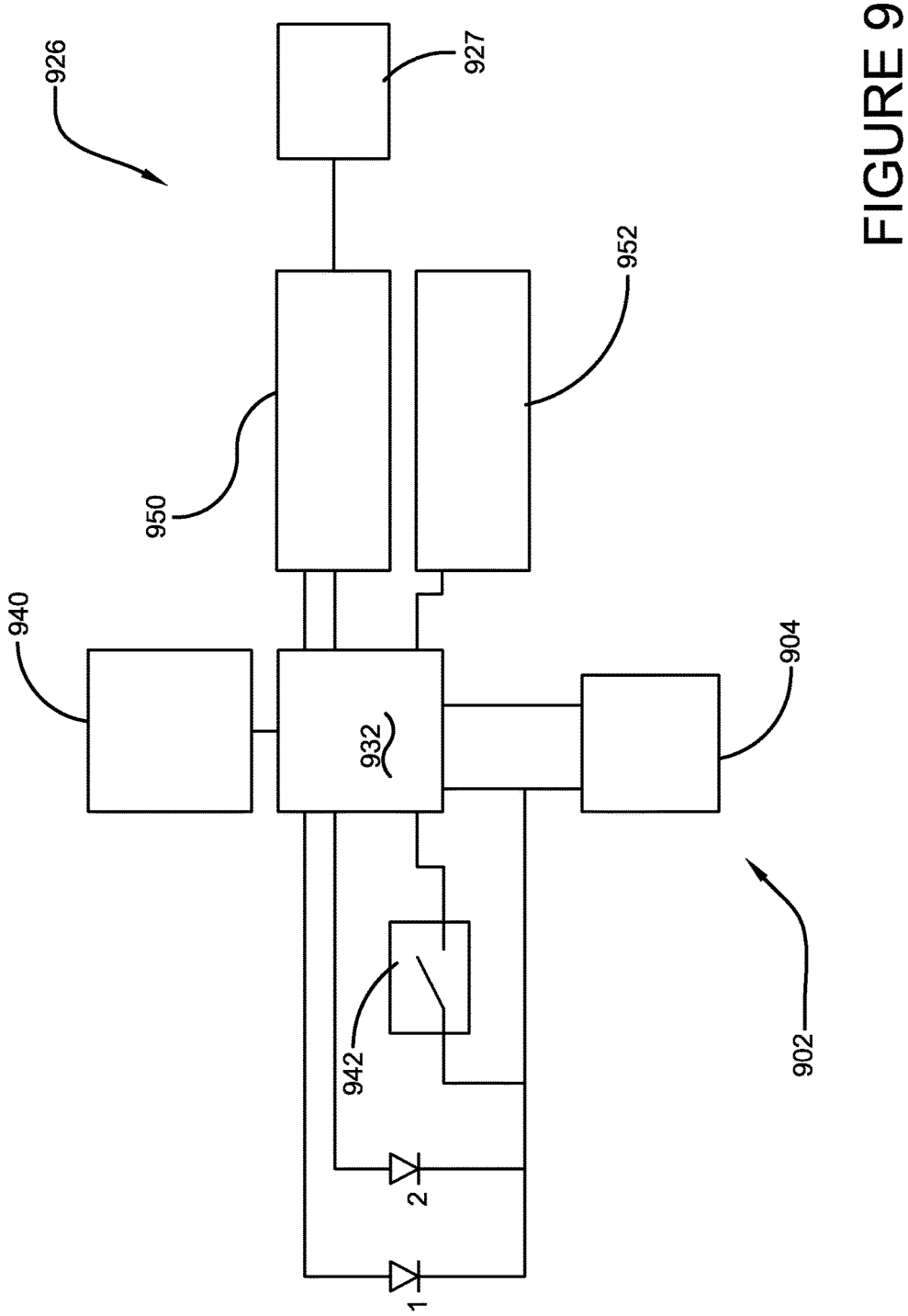
FIG. 9 is a schematic drawing of one aspect of one or more portions of one or more systems described herein.

FIG. 9 is a schematic diagram of an exemplary implementation of a circuit that may be utilized in connection with the present invention. The example implementation of the electrical and mechanical components of the closure component 505 is illustrated. A power switch 942 may be in communication with a processor 932 (e.g., microcontroller). The access determination component 726, 926 may also be in communication with the processor 932. The access determination component may be the biometric reader 927 and a sensor interface board 950. A power source 952, such as a servo motor may be energized by a battery 904, which may also be in communication with the processor 932. In one implementation, the processor 932 and communication sensor 940 may be a TINY DUINO microcontroller (e.g., processor board) and TINYSHIELD respectively, both available from Akronsense, LLC dba TinyCircuits of Akron, Ohio.

Figure 10:
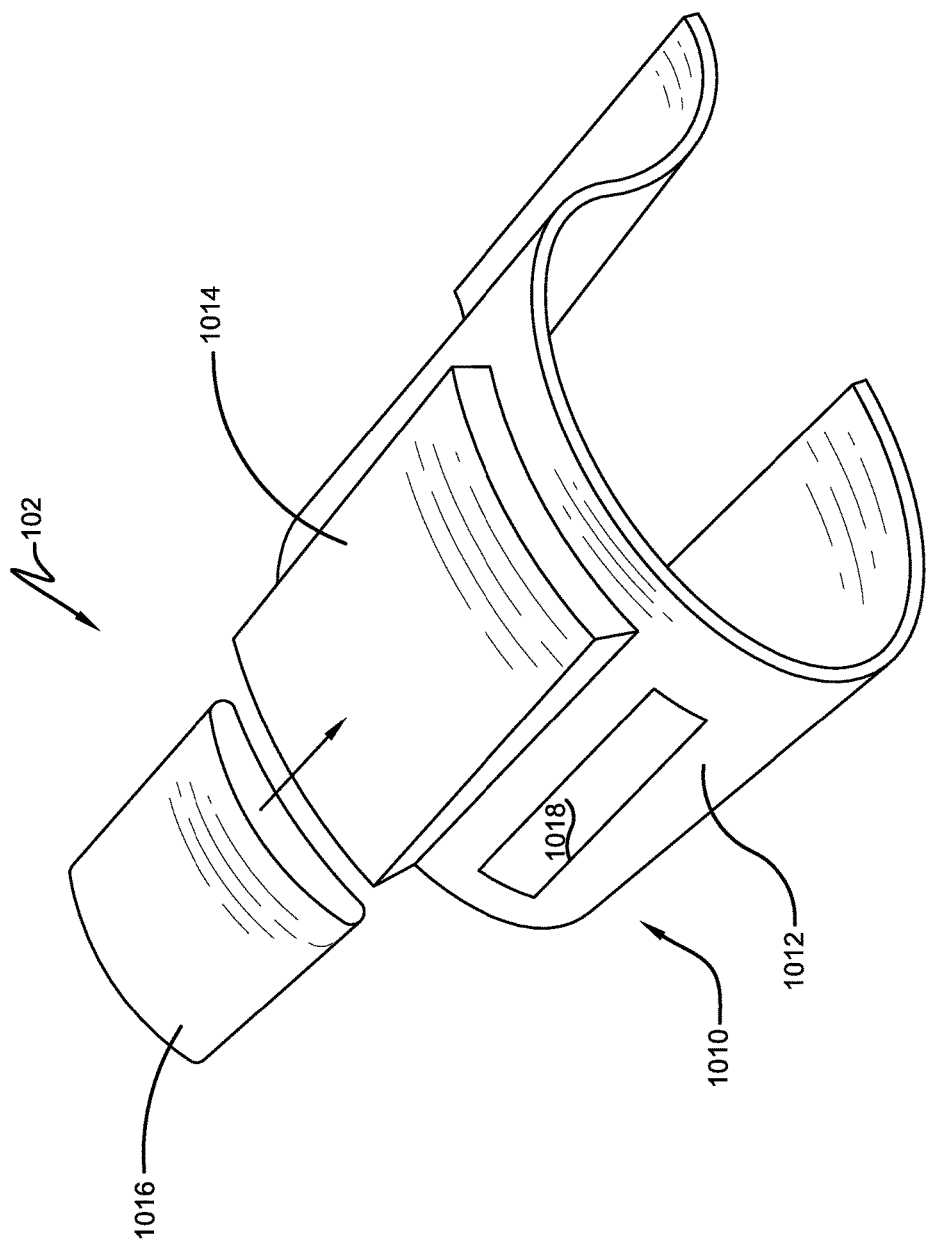
FIG. 10 is another implementation of one or more portions of one or more systems described herein.

FIG. 10 is another implementation of the present invention. In this implementation, the dispensing component 102 may have a body 1010 that may take the form of an adjustable band 1012 and may further comprise a housing 1014 selectively receiving a medicinal cartridge 1016. The adjustable band 1012 may be of flexible material, adjustable straps or even self-adhesive. The medicinal cartridge 1016 may have a mating port (not shown) to selectively engage and secure the medicinal cartridge 1016 to the housing 1014. In one implementation, the housing port (not shown) and the medicinal cartridge mating port (not shown) may have different configurations dependent upon the medications or material being dispensed. By means of nonlimiting examples, an antibiotic may have one configuration with the housing and the medicinal cartridge. Yet, insulin for a diabetic patient may have an entirely different configuration. Having different port configurations may help establish correct medicinal choices and dosages. In another implementation of the present invention, the medicinal cartridge 1016 may be positionably trackable such as through a global positioning system but is not limited thereto. The medicinal cartridge 1016 may also comprise a display 1018 for determining the level of dispensing the medication. In one implementation, the amount of material remaining in the dispenser may be displayed using a tracking downwards from not dispensed to fully dispensed. In another implementation, the display may display slightly dispensed to fully dispensed. In one implementation, the display for determining the level of dispensing the medication is a visual display. It may also be audio signal or a combination of both. The adjustable band may further comprise a power source, such as but not limited to a battery, to provide power to the memory device to transmit information via the notification system to the remote device. The medicine that may be disposed from the medicinal cartridge may be absorbed through the patient's skin.

With continued reference to FIG. 10, in one implementation, the following steps may be undertaken by a user. The user may attach the band to an area of his or her body, such as an arm but not limited thereto. The medicinal cartridge may then be inserted into the housing port. An audible or visual indicator may alert the user of successful placement of the medicinal cartridge, such as a green light. The medicine in the cartridge may then begin to dispense, and data may be sent to the communication component. As medicine continues to be dispensed, status data may be sent to the communication component. Upon a certain threshold of medicine being dispensed, such as about 50% (or possibly any percentage between about 40%-about 60%, another alert may be given, such as a yellow light. Dispensing data may be sent to the communication component. Upon completion of dispensing, another indicator, such as a red light may be provided. The band may then be removed from the user by themselves or through a second authorized user. It should be understood that the status of data transmission may be continuous, intermittent, upon command (e.g. push/pull notifications) or any combination thereof.

Figure 11A:
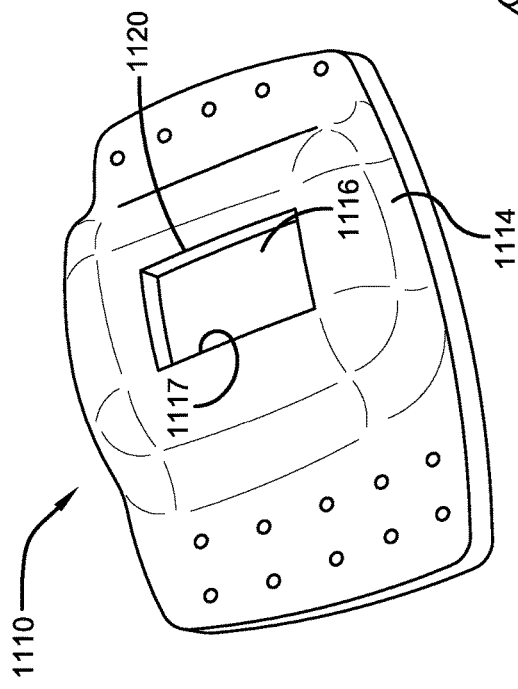
FIG. 11A is another implementation of one or more portions of one or more systems described herein.

With reference to FIG. 11A, another implementation of the present invention is illustrated. In this nonlimiting implementation of the present invention, the dispensing component may take the form of a transdermal material for delivery of medicine. The body 1110 may be a band 1114 of various sizes that may dispense material and communicate data to the notification component. The band may be a variety of colors. An underside of the band may have an adhesive to securely attach the band to an area of the user's body, such as an arm or leg or other body area. The material of the band 1114 may be such that it is flexible and can conform to the unique curves, bends and muscle contours of the user. The material on the band 1114 may be delivered by direct contact to a surface that is not similar to the band device, such as without limitation, a user's skin. The material may also be delivered through a medicinal cartridge 1116 or other port 1117. A power source can power a data component to transmit data about the status of material dispensing to the communication component. Data transmitted to the communication component may include without limitation, data, material dispensation status, events and location. A status indicator 1120 may be utilized to provide an operational condition, such as but not limited to, status of the material being dispensed. The status indicator may be audible or visual. If in visual form it may be a color indicator or it could be an image, such as a character or logo. The image may increase (darken) or decrease (lighten) as the material is delivered.

Figure 11B:
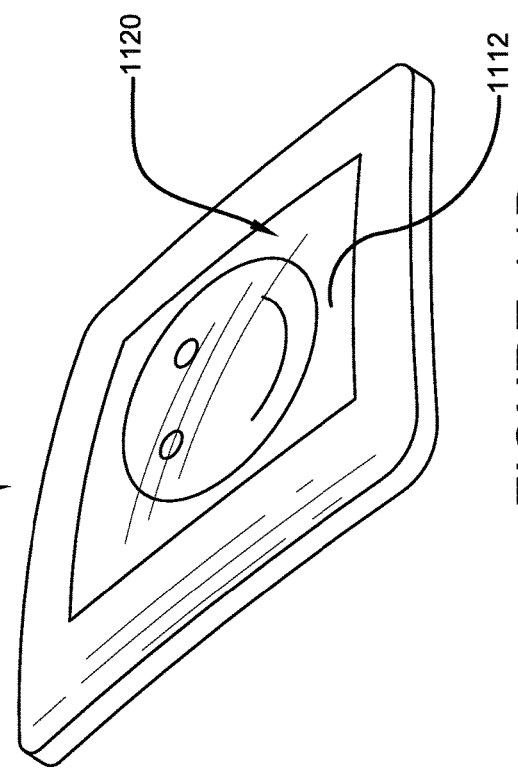
FIG. 11B is another implementation of the one or more portions of one or more systems described herein.

With reference to FIG. 11B, another implementation of the present invention is shown. The body 1110 may not be operably connected with communication component the. As material is dispensed, an image 1112 may appear or disappear indicated the status of material being dispensed. By way of nonlimiting example, the body 1110 may be affixed to a child's arm. As the medication dispenses, a cartoon character image may visually appear on the body 1110. As the medicine continues to dispense, the image may become darker. It is also contemplated to be within the scope of the invention that the image may lighten as material is dispensed. In another implementation, the image may change (e.g. a sad face to a happy face). Once the material has completed being dispensed, the user may remove the body 1110 from his or her body area.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Reference throughout this specification to "one implementation" or "an implementation" means that a particular feature, structure, or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A system for medicine dosage compliance, comprising:
   a personal, portable dispensing component that holds medicine, and that provides for the medicine to be dispensed based at least upon authorized identification of both a user and a secondary authorizer, the dispensing component comprising a biometric identity authentication component that automatically authenticates a biometric identity of both the user and the secondary authorizer at the time of a dispensing event; and
   a communication component engaged with the dispensing component, and providing data indicative of one or more notifications to one or more third parties, the communication component comprising:
   a wireless personal area networking component that sets up a local wireless personal area networking connection between the dispensing component and a local device to share data between the dispensing component and a local device, the local device separately, communicatively coupled to a remote network component; and
   a notification component that generates data indicative of notification information of the dispensing event for one or more third parties.

2. The system of claim 1, the dispensing component comprising an access determination component that determines access authorization for dispensing the medicine based on a rule set stored in one of:
   the access determination component; and
   the local device coupled with the dispensing component in the wireless personal area network.

3. The system of claim 2, the rule set comprising one or more of:
   dispensing schedule information;
   dispensing amount schedule information;
   authorized user information; and
   authorized secondary authenticator information.

4. The system of claim 2, the communications component comprising a message receiving component that receives:
   updates to the rule set; and
   alerts targeted to the user and/or the secondary authorizer.

5. The system of claim 4, the message receiving component receiving a message comprising authorization from a primary authorizer, the authorization from the primary authorizer authorizing access to the dispensing component to dispense medicine.

6. The system of claim 1, the communication component comprising the local device communicatively coupled to a remote network, the local device comprising at least a portion of the notification component and a predetermined list of third parties to which the one or more notifications are sent.

7. The system of claim 1, the one or more notifications comprising one or more of:
   a notification to a primary authorizer that the dispensing component was accessed and/or re-secured after access;

a notification to a predetermined clinician that the dispensing event has occurred;
a notification to a predetermined pharmacy that the dispensing event has occurred;
a notification to a predetermined pharmacy of an expected amount of medicine remaining after the dispensing event has occurred;
a notification to a predetermined health care insurer that the dispensing event has occurred;
a notification to a predetermined electronic medical record that the dispensing event has occurred; and
a notification to a predetermined third party that the dispensing event has occurred.

8. The system of claim 1, the notification component notifying the one or more third parties of an unauthorized access attempt.

9. The system of claim 1, the identity authentication component comprising a fingerprint reader that captures a fingerprint biometric marker of the user and/or the secondary authorizer.

10. The system of claim 1, the identity authentication component comprising data storage that stores authentication data associated with at least the user and the secondary authorizer.

11. The system of claim 1, the dispensing component further comprising:
a container; and
a lockable cap selectively removable from the container.

12. The system of claim 11, wherein the lockable cap further comprises:
a power device; and
a locking pin operatively connected to the power device, the locking pin having a first position and a second position.

13. The system of claim 12, wherein the power device is a servo motor.

14. The system of claim 12, wherein the first position is a locked position and the second position is an unlocked position.

15. The system of claim 11, wherein the lockable cap further comprises an alignment sensor to detect if the lockable cap is in a locked position or an unlocked position, alignment sensor to communicate with notification system to provide alert messaging.

16. The system of claim 12, the lockable cap further comprising a rechargeable battery to energize the power device.

17. A medicine dispensing device, comprising:
a closure component that selectably engages with a personal, portable medicine dispensing container to close an opening to the medicine dispensing container;
a biometric reader engaged with the closure component to read one or more biometric markers both of a user and a secondary authorizer;
an authentication component communicatively coupled with the biometric reader to authenticate an identity of both the user and the secondary authenticator based upon the one or more biometric markers, the closure component providing access to the opening to the medicine dispensing container upon authentication of both the user and the secondary authenticator at a time of a dispensing event based at least upon a dispensing rule set;
a communication component engaged with the closure component to identify the dispensing event and communicate data indicative of the dispensing event to a local computing device, communicatively coupled with the communication component through a wireless personal area network, the computing device remotely communicatively coupled with a remote computing component to communicate the data indicative of the dispensing event to the remote computing component; and
the remote computing component receiving the data indicative of the dispensing event and transmitting data indicative of a notification of the dispensing event to one or more third parties associated with the user, and the remote computing component transmitting an update to the dispensing rule set.

* * * * *